(12) United States Patent
Nelson et al.

(10) Patent No.: US 8,227,652 B2
(45) Date of Patent: Jul. 24, 2012

(54) SYNTHESIS OF PROPYLBENZENE FROM TOLUENE AND ETHYLENE

(75) Inventors: Robert W. Nelson, League City, TX (US); Christopher A. Curtis, Houston, TX (US); Stephen E. Belmont, Baton Rouge, LA (US)

(73) Assignee: Albemarle Corporation, Baton Rouge, LA (US)

( * ) Notice: Subject to any disclaimer, the term of this patent is extended or adjusted under 35 U.S.C. 154(b) by 225 days.

(21) Appl. No.: 12/532,651

(22) PCT Filed: Mar. 27, 2008

(86) PCT No.: PCT/US2008/058373
§ 371 (c)(1),
(2), (4) Date: Jan. 21, 2010

(87) PCT Pub. No.: WO2008/121679
PCT Pub. Date: Oct. 9, 2008

(65) Prior Publication Data
US 2010/0145121 A1   Jun. 10, 2010

(51) Int. Cl.
*C07C 2/72* (2006.01)
(52) U.S. Cl. ...................................................... 585/452
(58) Field of Classification Search .................... 585/452
See application file for complete search history.

(56) References Cited

U.S. PATENT DOCUMENTS
4,950,831 A   8/1990   Staton et al.

FOREIGN PATENT DOCUMENTS
FR   2 703 678   10/1994
GB   1 269 280   4/1972

*Primary Examiner* — Thuan Dinh Dang
(74) *Attorney, Agent, or Firm* — Marcy M. Hoefling; Jeremy J. Kliebert; James A. Jubinsky

(57) ABSTRACT

Methods are provided for producing alkylbenzenes, such as propylbenzene, from aromatics, such as toluene, and alkenes, such as ethylene. Such methods comprise combining the toluene with about 100 ppm to about 350 ppm water and alkali metal catalyst, activating the catalyst at about 180° C. to about 220° C., adding the ethylene and conducting the synthesis reaction at about 130° C. to about 150° C.

2 Claims, 1 Drawing Sheet

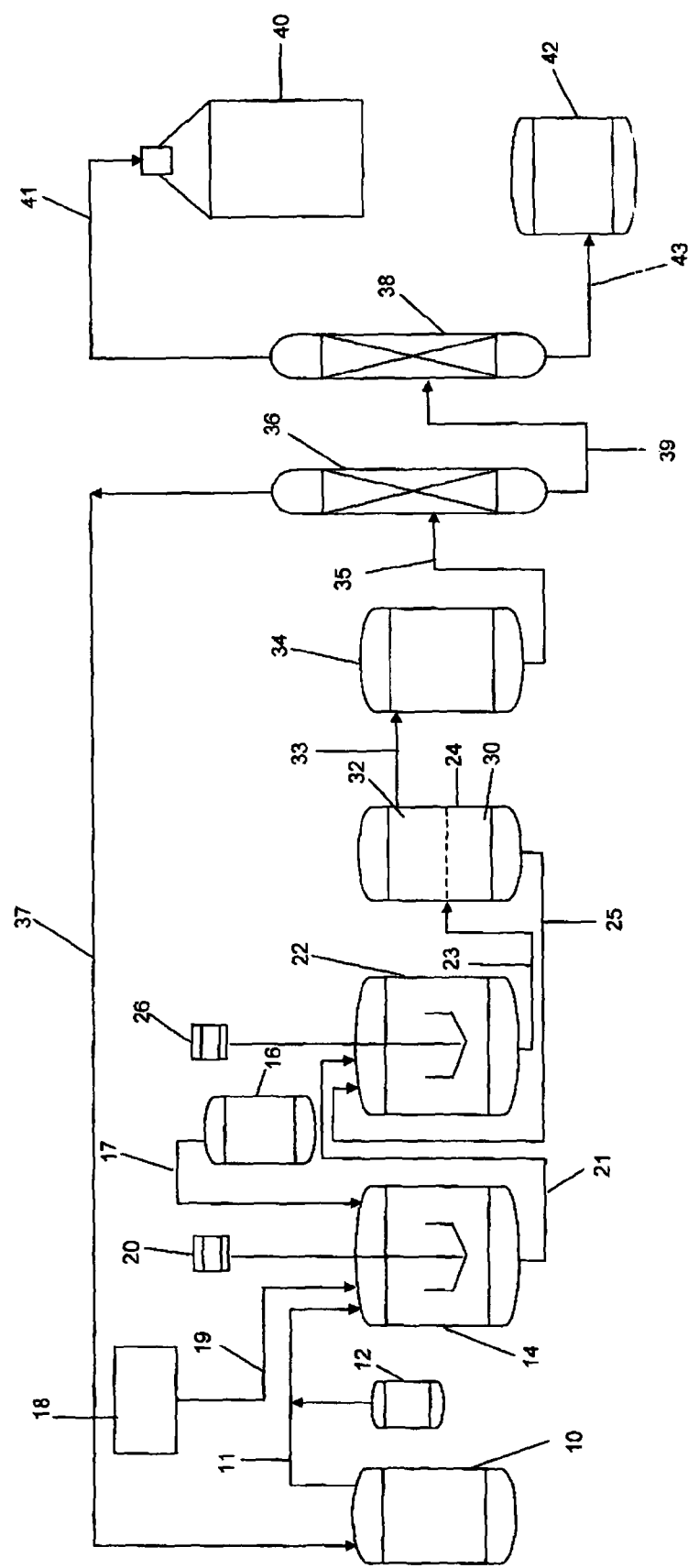

SYNTHESIS OF PROPYLBENZENE FROM TOLUENE AND ETHYLENE

BACKGROUND

Alkylbenzenes are useful, for example, as intermediates in the production of various end products. It is known that alkali metals, when reacted with alkylbenzenes, will displace benzylic hydrogens. The resulting alkylbenzene anion/alkali metal cation pair will undergo a reaction with olefins at certain temperatures to give alkylation products in which some or all saturated benzylic carbon atoms are alkylated in such a way as to replace some or all of the benzylic hydrogen atoms on a carbon atom with one aliphatic chain per benzylic hydrogen atom. Such reactions can yield a variety of products, depending on the number of saturated benzylic carbon atoms and the number of hydrogen atoms on a given benzylic carbon atom. In the commercial production of alkylbenzenes, a product of high purity is generally desired, and byproducts must be removed. Several patents and publications address issues related to providing suitable methods for commercial production of alkylbenzenes. See, e.g., U.S. Pat. No. 4,950,831 and U.S. Pat. No. 6,100,437.

A particular alkylbenzene, propylbenzene, can be used, e.g., in textile dyeing and printing, as a solvent for cellulose acetate in the manufacture of methylstyrene, and in various consumer products.

Various methods for production of propylbenzene are published in the literature. For example, publications indicate that propylbenzene can be made by alkylation of benzene with cyclopropane, by isomerization of cumene using zeolite, by Friedel-Crafts acylation of benzene with propionyl chloride, or by reaction of toluene and ethylene using NaK.

In spite of these publications, and efforts by others to improve the production of alkylbenzenes, to our knowledge propylbenzene is not widely produced commercially in significant quantities. Thus, economically-efficient methods that provide propylbenzene products of commercially suitable purity are needed.

THE INVENTION

This invention meets the above-described needs by providing methods comprising (a) combining at least aromatic hydrocarbon having an active hydrogen on a saturated alpha-carbon, water in an amount such that the water content is in the range of more than 100 ppm to about 350 ppm based on the content of the water and the aromatic hydrocarbon, and alkali metal to form a mixture; (b) maintaining the mixture at about 180° C. to about 220° C. for at least about 30 minutes; (c) cooling the mixture to about 150° C. to about 130° C.; (d) combining at least the mixture and alkene to form a reaction mixture; (e) maintaining the reaction mixture at about 130° C. to about 150° C. for longer than about 1 hour while agitating the reaction mixture at about 150 psig to about 300 psig; and (f) producing alkylbenzene. Further such methods are provided comprising (g) recovering from the reaction mixture unreacted aromatic hydrocarbon having an active hydrogen on a saturated alpha-carbon; and wherein at least a portion of the recovered unreacted aromatic hydrocarbon is used in (a). Also provided are methods comprising (a) combining at least toluene, water in an amount such that the water content is in the range of more than 100 ppm to about 350 ppm based on the content of the water and the toluene, and sodium-potassium alloy to form a mixture; (b) maintaining the mixture at about 180° C. to about 200° C. for at least about 30 minutes; (c) cooling the mixture to about 150° C. to about 130° C.; (d) combining at least the mixture and ethene to form a reaction mixture; (e) maintaining the reaction mixture at about 130° C. to about 150° C. for longer than about 1 hour while agitating the reaction mixture at about 150 psig to about 300 psig; (f) producing propylbenzene; and such methods are provided comprising (g) recovering from the reaction mixture unreacted toluene; and wherein at least a portion of the recovered unreacted toluene is used in (a).

FIGURE

The invention will be better understood by reference to FIG. 1, which is a process flow diagram representative of methods according to this invention.

AROMATIC HYDROCARBON

The aromatic hydrocarbon having an active hydrogen on a saturated alpha-carbon may be any such compound that is known to be useful in such reactions, such as toluene, ethylbenzene, n-propylbenzene (NPB), isopropylbenzene, n-butylbenzene, sec-butylbenzene, isobutylbenzene, n-eicosylbenzene, o-, m-, and p-xylenes, o-, m-, and p-ethyltoluenes, 1,3,5-trimethylbenzene, 1,2,4,5- and 1,2,3,5-tetramethylbenzenes, p-diisopropylbenzene, 1- and 2-methylnaphthalenes, dimethylnaphthalenes, 1-ethyl-4-n-octadecylnaphthalene, 1,4-di-n-pentylnaphthalene, 1,2,3,4-tetrahydronaphthalene, indan, cyclohexylbenzene, methylcyclohexylbenzene, diphenylmethane, etc. However, it is generally a hydrocarbon corresponding to the formula RR'R"CH, in which R is an aryl group of up to 20 carbons and each of R' and R" is independently selected from hydrogen and alkyl and aryl groups of up to about 20 carbons. The aromatic hydrocarbon typically comprises alkylbenzene having one or more ar-alkyl groups. A particularly suitable aromatic hydrocarbon is toluene.

Alkali Metal

As is known to those skilled in the art (see e.g., Cobb), alkali metal employed as a catalyst may be lithium, stadium, potassium, rubidium, or cesium; and it appropriately has its surface area increased by being finely divided or liquid. Particularly suitable alkali metals are potassium or potassium alloy, e.g., sodium-potassium alloy. A suitable alkali metal comprises sodium-potassium alloy having a potassium content of about 40 wt % to about 90 wt %. The amount of alkali metal used is a catalytic amount, generally about 2 mol % to about 10 mol %, based on the amount of either of the reactants when they are employed in equimolar amounts or on the amount of the major reactant when they are not utilized in equimolar amounts.

Alkene

The alkene that is used in the practice of the invention may be any of the alkenes that are known to be useful in such reactions, such as ethene, propene, 1-butene, 2-butene, isobutene, 1-pentene, 2-pentene, 3-methyl-1-butene, 2-methyl-2-butene, 1-hexene, 2-hexene, 3-hexene, 4-methyl-1-pentene, 3-methyl-1-pentene, 4-methyl-2-pentene, 1-heptene, 2-heptene, 2-octene, 4-nonene, 1-decene, 2-decene, 1-dodecene, 3-tetradecene, 5-hexadecene, 6-methyl-4-heptadecene, 1-eicosene, etc. However, it is generally alkene corresponding to the formula QQ'C=CTT', in which each of Q, Q', T, and T' is independently selected from hydrogen and alkyl groups of up to about 20 carbons. The alkene typically comprises up to about 20 carbons. Particularly suitable alkenes are ethylene and propylene.

DESCRIPTION

Referring to FIG. 1, methods according to this invention can comprise combining aromatic hydrocarbon as described herein, such as toluene, from container 10 (via line 11) and water from container 12 in reaction vessel 14. If desired, as is shown in FIG. 1, water from container 12 can be fed into reaction vessel 14 via line 11. Also, dispersant, such as tall oil, can be fed from container 12, via line 11 if desired, into reaction vessel 14. The water content fed into reaction vessel 14 can be in the range of more than 100 ppm to about 350 ppm based on the total content of the water plus the aromatic hydrocarbon. The water content can range from about 260 ppm to about 350 ppm, or from about 300 ppm to about 330 ppm. The water fed from container 12 can be from any suitable source and is typically potable water. Alkali metal, such as sodium-potassium alloy, can be fed from container 16, via line 17, into reaction vessel 14. The combination/mixture of toluene, water, tall oil, and sodium-potassium alloy within reaction vessel 14 can be heated and maintained at about 180° C. to about 220° C. for at least about 30 minutes. In most cases, maintaining the combination at 180° C. to about 220° C. for longer than about 5 or 6 hours would destroy the catalyst. After the mixture in reaction vessel 14 is maintained within the desired temperature range for the desired time period, the mixture can be cooled to about 150° C. to about 130° C. An alkene as described herein, such as ethylene, can be fed into reaction vessel 14 from container 18 via line 19 and combined with the mixture to form a reaction mixture. The reaction mixture in reaction vessel 14 can be maintained at about 130° C. to about 150° C., or from about 138° C. to about 140° C., and about 150 psig to about 300 psig, for longer than one hour while being agitated by action of agitator 20. Agitator 20 can be any suitable agitator, e.g., a flat pitch impeller. The reaction mixture can be transferred from reaction vessel 14 to quench vessel 22 via line 21. Quench water from a suitable source (not shown) can be added to quench vessel 22, and/or recycle quench water from container 24 can be fed to quench vessel 22 via line 25. The reaction mixture and quench water/recycle quench water in quench vessel 22 can be agitated by action of agitator 26. Quenched reaction mixture can be transferred from quench vessel 22 to settling phase vessel 24 via line 23. In settling phase vessel 24, aqueous phase 30 separates from organic phase 32. Aqueous phase 30 can be recycled via line 25 to quench vessel 22 as recycle quench water. Build up of caustics in recycled quench water can result in less residual aromatics in aqueous phase 30 when separated from organic phase 32, than would otherwise be present in aqueous phase 30. Organic phase 32 from settling phase vessel 24 can be transferred to distillation feed vessel 34 via line 33. Organics from distillation feed vessel 34 can be fed to distillation column 36 via line 35. Unreacted aromatic hydrocarbon, e.g., toluene, can be fed/recycled to container 10 via line 37. Heavy organics from distillation column 36 can be transferred to distillation column 38 via line 39. Produced alkylbenzene, such as n-propylbenzene, can be transferred from distillation column 38 to product storage container 40 via line 41. Heavy organics from distillation column 38 can be transferred to bottoms container 42 via line 43.

The chemical reaction when toluene and ethylene are used in methods of this invention to produce propylbenzene can be shown as follows:

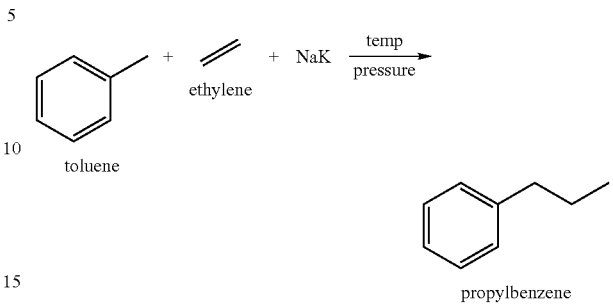

Examples

The following examples are illustrative of the principles of this invention. It is understood that this invention is not limited to any one specific embodiment exemplified herein, whether in the examples or the remainder of this patent application.

In the examples listed in Table 1, the following method was used, except as otherwise indicated. Toluene in the amount shown and water in an amount such that the water content was in the range of more than about 100 ppm to about 350 ppm based on the content of the water and the toluene, and NAK in the amount shown were combined to form a mixture. Tall oil was added as a dispersant. The mixture was heated and maintained at the temperature, and for the time period, shown in the column headed "Catalyst Activation temp & time". The mixture was cooled to within the temperature range shown in the column headed "Temp range" and ethylene was added to the cooled mixture in the amount shown to form a reaction mixture. The reaction mixture was maintained within the temperature range shown in the column headed "Temp range" for the time shown in the column headed "Rxn time" while the reaction mixture was agitated. Product ratio (GC area %) data is given for toluene and n-propylbenzene (NPB), as well as for side products 3-phenylpentane (3-PP) and Indan. A flat pitch impeller was used to create high shear agitation. Note that in example ID's 19-21, insufficient water was used (i.e., less than 100 ppm water based on the content of the water and the toluene as determined by Karl-Fischer analysis). In example ID 26, too much water was used (i.e., more than 350 ppm water based on the content of the water and the toluene as determined by Karl-Fischer analysis).

TABLE 1

| ID | Toluene charge (lbs) | NaK charge (lbs) | Ethylene Charge (lbs) | Catalyst Activation temp (° C.) & time | Temp setpoint (° C.) | Temp range (° C.) | Pressure setpoint (° C.) | Pressure range (psig) | Rxn time (hr) | Product ratio (GC area %) | | | |
|---|---|---|---|---|---|---|---|---|---|---|---|---|---|
| | | | | | | | | | | Toluene | NPB | 3-PP | Indan |
| 1 | 25000 | 125 | 1023 | 180 - 1 hr | 140 | 140-145 | 270 | 300 | 2 | 99.3 | 0.5 | 0 | 0 |
| 2 | 25000 | 125 | 3000 | 175-180 - 1 hr; 70-180 - 3 hr | 140-145 | 129-157 | 270-300 | 260-310 | 4 | 72.8 | 21.7 | 4.5 | 0.08 |
| 3 | 25000 | 125 | 5500 | 175-180 - 1 hr | 145-175 | 145-175 | 270-300 | 260-300 | 5 | 47.3 | 27.7 | 20.9 | 0.32 |
| 4 | 25000 | 180 | 2765 | 171-177 - 1 hr | 150-155 | 150-165 | 300-350 | 300-352 | 3 | 71.3 | 18.6 | 7.8 | 0.20 |

TABLE 1-continued

| ID | Toluene charge (lbs) | NaK charge (lbs) | Ethylene Charge (lbs) | Catalyst Activation temp (° C.) & time | Temp setpoint (° C.) | Temp range (° C.) | Pressure setpoint (° C.) | Pressure range (psig) | Rxn time (hr) | Product ratio (GC area %) Toluene | NPB | 3-PP | Indan |
|----|----|----|----|----|----|----|----|----|----|----|----|----|----|
| 5 | 25000 | 125 | 5501 | ~200 - 2.5 hr | 145 | 140-145 | 300 | 285-300 | 2 | 43.1 | 39.9 | 15.0 | 0.24 |
| 6 | 25000 | 125 | 5500 | 200 - 6 hr; 145 - 2 hr | 145 | 145-146 | 300 | 297-300 | 3 | 43.3 | 37.0 | 16.0 | 0.62 |
| 7 | 25000 | 132 | 5501 | 200 - 2 hr | 145 | 144-146 | 300 | 299-302 | 1.8 | 40.2 | 44.4 | 13.7 | 0.15 |
| 8 | 25400 | 100 | 4500 | 200 - 2 hr | 145 | 144-146 | 300 | 299-305 | 4 | 54.9 | 30.8 | 11.6 | 0.34 |
| 9 | 25000 | 130 | 5500 | 200 - 2 hr | 145 | 144-146 | 300 | 300 | 1.8 | 39.3 | 48.3 | 12.0 | 0.11 |
| 10 | 25000 | 125 | 5500 | 200 - 2 hr | 145 | 144-147 | 300 | 300 | 2.3 | 40.4 | 42.7 | 15.4 | 0.09 |
| 11 | 25000 | 130 | 5500 | 200 - 2 hr | 145 | 145-147 | 300 | 300-302 | 1.7 | 40.5 | 42.3 | 15.5 | 0.10 |
| 12 | 25000 | 133 | 5500 | 200 - 2 hr | 145 | 141-148 | 300 | 299-302 | 1.7 | 41.0 | 42.8 | 14.9 | 0.08 |
| 13 | 25000 | 131 | 5500 | 200 - 2 hr | 145 | 143-148 | 300 | 299-301 | 1.8 | 42.3 | 39.0 | 17.1 | 0.08 |
| 14 | 25000 | 132 | 5500 | 200 - 2 hr | 145 | 144-149 | 300 | 272 | 1.3 | 41.6 | 40.2 | 16.6 | 0.03 |
| 15 | 25000 | 130 | 5500 | 200 - 2.5 hr | 145 | 145-150 | 300 | 270 | 1.3 | 42.5 | 41.0 | 15.1 | 0.10 |
| 16 | 25000 | 130 | 5400 | 200 - 2.5 hr | 142 | 140-147 | 300 | 301 | 1.3 | 40.5 | 44.8 | 13.4 | 0.10 |
| 17 | 25000 | 130 | 5500 | 200 - 2.5 hr | 140 | 138-144 | 300 | 302 | 1.7 | 39.3 | 46.5 | 12.6 | 0.11 |
| 18 | 25000 | 130 | 5500 | 200 - 2.5 hr | 140 | 138-143 | 300 | 303 | 1.9 | 38.6 | 46.6 | 13.5 | 0.02 |
| 19 | 25000 | 130 | 5500 | 200 - 2.5 hr | 140 | 137-144 | 300 | 302 | 1.7 | 40.8 | 41.9 | 16.0 | 0.07 |
| 20 | 25000 | 130 | 5500 | 200 - 2.5 hr | 140 | 138-144 | 300 | 300 | 1.3 | 42.7 | 38.1 | 17.7 | 0.02 |
| 21 | 25000 | 130 | 5500 | 200 - 2.5 hr | 138 | 136-143 | 300 | 272 | 1.2 | 41.7 | 38.6 | 18.1 | 0.09 |
| 22 | 25000 | 130 | 5500 | 200 - 2.5 hr | 138 | 135-142 | 300 | 300 | 1.5 | 39.0 | 45.3 | 14.1 | 0.15 |
| 23 | 25000 | 130 | 5500 | 200 - 2.5 hr | 138 | 135-142 | 300 | 300 | 1.9 | 38.3 | 47.8 | 12.4 | 0.14 |
| 24 | 25000 | 130 | 5500 | 200 - 2.5 hr | 138 | 135-142 | 300 | 300 | 2.0 | 39.8 | 46.1 | 12.6 | 0.13 |
| 25 | 25000 | 130 | 5500 | 200 - 2.5 hr | 138 | 135-142 | 300 | 300 | 2.1 | 37.6 | 48.7 | 12.2 | 0.03 |
| 26 | 25000 | 130 | 5500 | 200 - 2.5 hr | 138 | 135-140 | 300 | 300 | 5.9 | 46.5 | 36.3 | 14.2 | 0.25 |
| 27 | 25400 | 130 | 5500 | 200 - 2.5 hr | 140 | 136-140 | 300 | 300 | 2.8 | 38.5 | 47.9 | 12.1 | 0.02 |
| 28 | 25000 | 130 | 5500 | 200 - 2.5 hr | 138 | 137-139 | 300 | 300 | 2.7 | 39.6 | 47.1 | 11.6 | 0.13 |
| 29 | 25000 | 130 | 5500 | 200 - 2.5 hr | 138 | 137-139 | 300 | 300 | 3.6 | 38.9 | 47.0 | 12.4 | 0.14 |
| 30 | 25000 | 130 | 5500 | 200 - 2.5 hr | 138 | 137-139 | 300 | 300 | 2.5 | 35.4 | 51.0 | 12.3 | 0.09 |
| 31 | 25000 | 130 | 5500 | 200 - 2.5 hr | 138 | 137-139 | 300 | 300 | 3.5 | 37.6 | 48.9 | 12.1 | 0.02 |
| 32 | 25000 | 130 | 5500 | 200 - 2.5 hr | 138 | 137-139 | 300 | 300 | 2.5 | 38.1 | 48.2 | 12.2 | 0.12 |
| 33 | 25000 | 130 | 5500 | 200 - 2.5 hr | 138 | 137-139 | 300 | 300 | 2.2 | 37.6 | 48.1 | 12.3 | 0.12 |
| 34 | 25000 | 130 | 5500 | 200 - 2.5 hr | 138 | 137-139 | 300 | 300 | 2.8 | 37.7 | 48.2 | 12.4 | 0.13 |
| 35 | 25000 | 117 | 5500 | 200 - 2.5 hr | 138 | 137-139 | 300 | 300 | 5.5 | 44.2 | 38.4 | 14.7 | 0.22 |

In example ID 1, the reactor was wet. In example ID's 2-4 there was poor catalyst activation. In example ID 6, the catalyst was heated for too long. In example ID 8, insufficient NaK was used.

Advantages to this invention, in addition to good recovery of alkylbenzene with low levels of impurities, include recycle of unreacted toluene. Quench water can also be reused.

It is to be understood that the reactants and components referred to by chemical name or formula anywhere in the specification or claims hereof, whether referred to in the singular or plural, are identified as they exist prior to being combined with or coming into contact with another substance referred to by chemical name or chemical type (e.g., another reactant, solvent, or etc.). It matters not what chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, combined, blended or mixed with one or more other substances, components and/or ingredients in accordance with the present disclosure. Whatever transformations, if any, which occur in situ as a reaction is conducted is what the claim is intended to cover. Thus the fact that a substance, component or ingredient may have lost its original identity through a chemical reaction or transformation during the course of contacting, combining, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

While the present invention has been described in terms of one or more preferred embodiments, it is to be understood that other modifications may be made without departing from the scope of the invention, which is set forth in the claims below.

What is claimed is:

1. A method comprising:
   (a) combining at least
       toluene,
       water in an amount such that the water content is in the range of more than 100 ppm to about 350 ppm based on the content of the water and the toluene, and
       sodium-potassium alloy
       to form a mixture;
   (b) maintaining the mixture at above 180° C. to about 220° C. for at least about 30 minutes;
   (c) cooling the mixture to about 150° C. to about 130° C.;
   (d) combining at least the mixture and ethene to form a reaction mixture;
   (e) maintaining the reaction mixture at about 130° C. to about 150° C. for longer than about 1 hour while agitating the reaction mixture with a high shear impeller at about 150 psig to about 300 psig;
   (f) producing propylbenzene.

2. The method of claim 1, further comprising:
   (g) recovering from the reaction mixture unreacted toluene;
   and wherein at least a portion of the recovered unreacted toluene is used in (a).

* * * * *